United States Patent [19]

Trost et al.

[11] Patent Number: 5,739,396

[45] Date of Patent: Apr. 14, 1998

[54] ASYMMETRIC LIGANDS USEFUL FOR TRANSITION METAL CATALYZED BOND FORMING REACTIONS

[75] Inventors: Barry M. Trost, Los Altos Hills; David L. Van Vranken, Irvine; Richard C. Bunt, Redwood City, all of Calif.

[73] Assignee: Stanford University, Stanford, Calif.

[21] Appl. No.: 487,039

[22] Filed: Jun. 7, 1995

Related U.S. Application Data

[63] Continuation-in-part of Ser. No. 308,839, Sep. 19, 1994, abandoned, which is a continuation-in-part of Ser. No. 804,783, Dec. 9, 1991, abandoned.

[51] Int. Cl.⁶ .................... C07F 9/28; C07F 9/50
[52] U.S. Cl. .................... 564/15; 548/412; 548/482; 549/6; 549/57; 549/216; 549/468; 549/469; 549/470
[58] Field of Search ................................ 564/15

[56] References Cited

U.S. PATENT DOCUMENTS 4,209,468  6/1980  Shulman .
4,705,895  11/1987  Okano et al. .

OTHER PUBLICATIONS

Morrison and Masler, *J. Org. Chem.*, 39:2, pp. 270–272 (1974).
Masuda and Stille, *J. Am. Chem. Soc.*, 100:1, pp. 268–272 (1978).
LaFont et al., *J. Chem. Research* (S), 234, p. 117 (1982).
Riley, *J. Organomet. Chem.*, 234, pp. 85–97 (1982).
MacNeil et al., *J. Am. Chem. Soc.*, 103, pp. 2273–2280 (1981).
Fryzuk and Bosnich, *J. Am. Chem. Soc.*, 99:19, pp. 6262–6267 (1977).
Roberts and Wild, *J. Am. Chem. Soc.*, 101:21, pp. 6254–6260 (1979).
Bergstein et al., *Synthesis*, 76, pp. 76–78 (1981).
Juge et al., *Tetrahedron Letters*, 31:44, pp. 6357–6360 (1990).
Imamoto et al., *J. Am. Chem. Soc.*, 112, pp. 5244–5252 (1990).
Knowles et al., *J. Am. Chem. Soc.*, 97:9, pp. 2567–2568 (1975).
Fukuda et al., *Tetrahedron Letters*, 31:49, pp. 7185–7188 (1990).
Onuma et al., *Chem. Letters*, pp. 905–908 (1979).
Achiwa, *J. Am. Chem. Soc.*, 98:25, pp. 8265–8266 (1976).
Beck and Menzel, *J. Organomet. Chem.*, 133, pp. 307–310 (1977).
Kagen and Dang, *J. Am. Chem. Soc.*, 94:18, pp. 6429–6433 (1972).
Aviron-Violet et al., *J. Mol. Catal.*, 5, pp. 41–50 (1979).
Dang et al., *J. Organomet. Chem.*, 91, pp. 105–115 (1975).
Glaser et al., *Tetrahedron Letters*, 52, pp. 4639–4642 (1977).
Kreufeld and Döbler, *React. Kinet. Catal. Lett.*, 16:2-3, pp. 229–232 (1981).

Pracejus and Pracejus, *J. Mol. Catal.*, 24, pp. 227–230 (1984).
Samuel et al., *Nouv. J. Chim*, 5:1, pp. 15–20 (1981).
Lauer et al., *J. Organomet. Chem.*, 177, pp. 309–312 (1979).
Tanaka et al., *Chem. Lett.*, pp. 1115–1118 (1975).
Alario et al., *J. Chem. Soc., Chem. Com.*, pp. 202–203 (1986).
Takaya et al., *Org. Syn.*, 67, pp. 20–32 (1989).
Grubbs and DeVries, *Tetrahedron Letters*, 22, pp. 1879–1880 (1977).
Trost and Murphy, *Organometallics*, 4, pp. 1143–1145 (1985).
Tamao et al., *Tetrahedron Letters*, 16, pp. 1389–1392 (1977).
Miyano et al., *Chem. Lett.*, pp. 729–730 (1980).
Miyano et al., *Bull. Chem. Soc. Jpn.*, 57, pp. 2171–2176 (1984).
Uehara et al., *Chem. Lett.*, pp. 441–444 (1983).
Hayashi et al., *Bull. Chem. Soc. Jpn.*, 53, pp. 1138–1151 (1980).
Hayashi and Kumada, *Acc. Chem. Res.*, 15, pp. 395–401 (1982).
Johnson et al., *J. Mol. Catal.*, 12, pp. 37–40 (1981).
Petit et al., *Nouv. J. Chim.*, 7:10, pp. 593–596 (1983).
Pracejus and Pracejus, *Tetrahedron Letters*, 39, pp. 3497–3500 (1977).
Fiorini et al., *J. Mol. Catal.*, 4, pp. 125–134 (1978).
Consiglio and Waymouth, *Chem. Rev.*, 89, pp. 257–276 (1989).
Noyori and Kitamura, "Enantioselective Catalysis with Metal Complexes. An Overview," in *Modern Synthetic Methods*, vol. 5, Scheffold, ed., Springer-Verlag: Berlin, pp. 115–198 (1989).
Noyori, *Chem. Soc. Rev.*, 18, pp. 187–208 (1989).
Ojima et al., *Tetrahedron Letters*, 45:22, pp. 6901–6939 (1989).
Blystone, *Chem. Rev.*, 89:8, pp. 1663–1679 (1989).

(List continued on next page.)

*Primary Examiner*—Johann Richter
*Assistant Examiner*—Jane C. Oswecki
*Attorney, Agent, or Firm*—Majestic, Parsons, Siebert & Hsue

[57] ABSTRACT

Ligands useful for transition metal catalyzed bond forming reactions are provided with a metal binding portion having at least one metal binding moiety

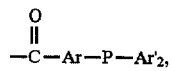

wherein Ar and Ar' each is an aryl or a heteroaryl. These ligands may be prepared by providing an aromatic carboxylic acid having a diarylphosphino or diheteroarylphosphino substituent on the aromatic ring, and forming an ester or an amide derivative of the carboxylic acid by coupling with a chiral diol or a chiral diamine. The ligands facilitate, for example, flexible strategies for enantiocontrolled construction of five membered carbocyclic rings with varying substitution patterns and high enantioselectivity.

10 Claims, No Drawings

OTHER PUBLICATIONS

Brunner, "Enantioselective Syntheses with Optically Active Transition Metal Catalysts," chapter 4 in *The Chemistry of the Metal–Carbon Bond*, vol. 5, Hartley, ed., John Wiley & Sons: New York, pp. 109–146 (1989).

Brunner, *Synthesis*, pp. 645–653 (1988).

Merlic, "Transition Metal Mediated Asymmetric Allylic Alkylations," chapter 2 in *Molybdenum Catalyzed Allylic Alkylations*, Ph.D. Dissertation, University of Wisconsin, Madison, pp. 78–79 (1988).

Kitamura et al., *Tetrahedron Letters*, 28:40, pp. 4719–4720 (1987).

Trost et al., *J. Am. Chem. Soc.*, 110, pp. 621–622 (1988).

Trost and Van Vranken, *J. Am. Soc.*, 113, pp. 6317–6318 (1991).

Fiorini and Giongo, *J. Mol. Catal.*, 5, pp. 303–310 (1979).

Trost and Van Vranken, *Angewandte Chemie*, 31:2, pp. 228–230 (1992).

Trost et al., *J. Am. Chem. Soc.*, 114, pp. 9327–9343 (1992).

Whiteshell, *Chem. Rev.*, 89, pp. 1581–1590 (1989).

ASYMMETRIC LIGANDS USEFUL FOR TRANSITION METAL CATALYZED BOND FORMING REACTIONS

This invention is a continuation-in-part of application U.S. Ser. No. 08/308,839, filed Sep. 19, 1994, abandoned, which is a continuation-in-part of U.S. Ser. No. 07/804,783, filed Dec. 9, 1991, abandoned.

This invention was made with Government support under Contract CHE-8706536 awarded by the National Science Foundation. The Government has certain rights in this invention.

FIELD OF THE INVENTION

The present invention generally relates to use of ligands for transition metal catalyzed reactions, and more particularly relates to a new class of asymmetric ligands preferably derived from 2-diphenylphosphinobenzoic acid as an ester or amide from chiral alcohols and chiral amines.

BACKGROUND OF THE INVENTION

The importance of enantiomerically pure compounds is a result of the enantiomeric selectivity of biology. Because biology is based on a particular enantiomer, L-amino acids, enantiomeric recognition is an inherent component of biological processes. A prototypical example of the enantiomeric selectivity is the case history of thalidomide. Thalidomide was a widely prescribed drug that was eventually removed from the market because of unforeseen side effects. Administered as a racemic mixture, the R-isomer is a sleep aid whereas the S-isomer is a potent teratogen. Thalidomide is not unique in having only one enantiomer of optically active compound that exhibits the desired pharmacological effect. However, because of the difficulties in synthesizing enantiomerically pure compounds, racemic mixtures are often used.

A relatively new and promising approach to enantioselective synthesis, where the chiral product is enriched in either enantiomer, is the use of optically active transition metal compounds as catalysts. Enantioselective catalysis in general hinges upon the ability to minimize the energy barrier (ΔΔG‡) of the desired enantiomer product relative to the other. Small energy differences translates into relatively large differences in enantiomeric excess. For example, a 1.3 kcal/mole difference in transition state energies results in an enantiomeric excess of 80%.

Enantiomeric excess ("e.e.") is the enrichment of one enantiomer over the other from the expected value. For example, if the optically active product contains equal amounts of enantiomers, then the enantiomeric excess is 0. If the ratio is 70:30, then the enantiomeric excess is 40%, and if the ratio is 90:10, then the enantiomeric excess is 80% and so on.

Transition metals are good candidates for enantioselective catalysis because of their ability to mediate a wide variety of bond-forming and bond-breaking processes. Because transition metals do not display the necessary specificity, the conjunctive use of chiral ligands or auxiliaries is essential for enantioselective catalysis. Coordinated to the metal, the metal-ligand complex binds to the prochiral precursor and in so doing induces the formation of one enantiomer over the other. Because both sterics and electronics are readily modified, phosphines are often preferred. As a result, a large number of chiral phosphine ligands have been prepared. However, only a few have gained popular use probably because of difficulties in synthesis or inadequate enantiomeric excesses or a combination of both.

One area where enantiomerically pure compounds are useful is where an enantiomerically pure vinylglycinol (or vinylglycine) is used as a synthetic building block for biologically important targets, such as various antibiotic enzyme inhibitors, calmodulin inhibitors, and others. EP 529,601, published Mar. 3, 1993, inventors Fuelling and Kretzschmar is an example of optically active vinylglycine compounds, useful as enzyme inhibitors, antibacterials, and cytostatics. These optically active vinylglycines are produced by enzymatically resolving racemic vinylglycine; however, a simple asymmetric synthesis that would provide access to both enantiomers is most desirable.

At present, the most effective synthesis of vinylglycine has begun with amino acids, which restricts ready availability to the L-enantiomer. A simple asymmetric synthesis providing access to each enantiomer, as desired, would be quite useful.

SUMMARY OF THE INVENTION

The present invention relates to a new class of ligands for enantioselective transition metal catalysis that can be easily and flexibly prepared for high levels of asymmetric induction.

In one aspect of the present invention, a ligand is provided that is useful for enantioselective transition metal catalysis and comprises a metal binding moiety that is attached to a chiral backbone. The chiral backbone is derived from a chiral alcohol or amine. The metal binding portion has at least one metal binding moiety with the structure

wherein Ar and Ar' each is an aryl or a heteroaryl with a single ring or fused rings. The ligand preferably has C2 symmetry and has two or three metal binding moieties per ligand molecule.

In another aspect of the present invention, a ligand is provided with a chiral backbone derived from a chiral carboxylic acid and a metal binding moiety has one of the two following structures

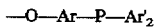

or

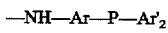

wherein Ar and Ar' each is an aryl or a heteroaryl with a single ring or fused rings. The ligand preferably also has C2 symmetry and has two or three metal binding moieties per ligand molecule.

In yet another aspect of the present invention, a method for preparing ligands useful for transition metal catalyzed bond forming reactions comprises providing an aromatic carboxylic acid having a diarylphosphino or diheteroarylphosphino substituent on the aromatic ring, and forming an ester or an amide derivative of the carboxylic acid by coupling with a chiral diol or a chiral diamine in the presence of dicyclohexylcarbodiimide.

In a further aspect of the present invention, a method for synthesizing cyclopentane analogs of carbohydrates comprises asymmetrically introducing heteroatoms around a cyclopentane nucleus of an intermediate while controlling the introduction by inducing an enantiomeric excess. Control is exercised by contacting the intermediate with a transition metal and a ligand for the transition metal. The ligand has a metal binding portion bound to a chiral scaffold. The chiral scaffold is derived from an asymmetric alcohol or an asymmetric amine. The metal binding portion is an aryl carboxylic acid derivative or a heteroaryl carboxylic acid derivative with a diarylphosphino or diheteroarylphosphino substituent on the aryl or on the heteroaryl moiety. The chirality of the ligand may be selected so as to correspond to the desired absolute stereochemistry induced in the transition metal catalyzed reaction.

A particularly preferred ligand of the invention has the Formula I structure, and is hereinafter sometimes referred to as "(RR)-$L_{12N}$," as an abbreviation of (–)-1R,2R-diamino-1N,2N-bis(2'-diphenylphosphino-1'-naphthoyl)cyclohexane.

FORMULA I

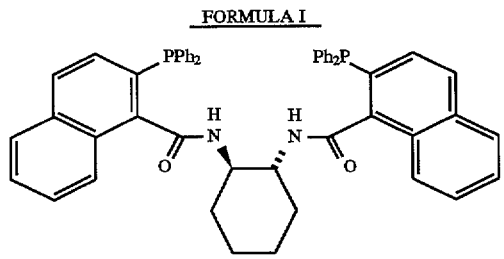

This chiral ligand embodiment has proved remarkably successful in the amination of butadiene monoepoxide, which is a potentially desirable starting material for an asymmetric synthesis providing access to each enantiomer of vinylglycinol. Thus, the ligand (RR)-$L_{12N}$ should prove useful in syntheses of many biologically important targets.

DETAILED DESCRIPTION OF THE PREFERRED EMBODIMENTS

Many ligands in accordance with the present invention give enantiomeric excesses ("e.e.") of about 75% or greater when tested in a relatively difficult transition metal catalyzed bond forming, five membered ring reaction. This e.e. test involves the ability of a chiral ligand to participate with palladium in a catalysis illustrated by Reaction 1 below.

REACTION 1

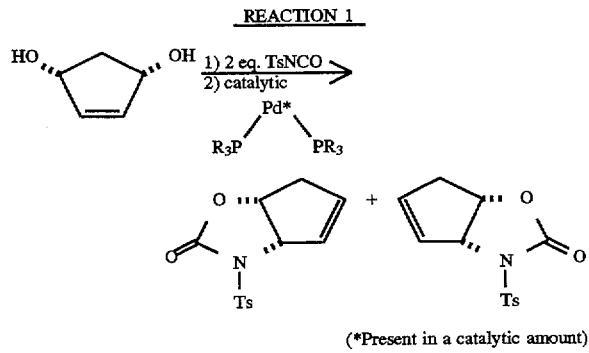

(*Present in a catalytic amount)

Unless otherwise indicated, the enantiomeric excesses obtained and reported herein will have been obtained with the cyclopentene diol substrate illustrated by Reaction 1. However, we have also obtained enantiomeric excesses through use of the inventive ligands in bond forming reactions involving substrates that are six and seven membered rings up to almost 100% (that is, obtaining reaction products that are substantially optically pure).

Transition metal catalyzed bond forming reactions (with which ligands in accordance with the invention are useful) are well known in the art, and among the recent reviews describing such reactions are:

(1) Consiglio et al., "Enantioselective Homogeneous Catalysis Involving Transition-Metal-Allyl Intermediates", *Chem. Rev.*, 1989, 89, 257–276;

(2) Noyori et al., "Enantioselective Catalysis with Metal Complexes. An Overview." *Modern Synthetic Methods*, Vol. 5, Scheffold, ed., Springer-Verlag: Berlin, 1989, 199–248;

(3) Noyori, R., "Chemical Multiplication of Chirality: Science and Applications," *Chem. Soc. Rev.*, 1989, 18, 1987–208;

(4) Ojima et al., "Recent Advances in Catalytic Asymmetric Reasons Promoted by Transition Metal Complexes", *Tetrahedron*, 1989, 45, 6901–6939;

(5) Blystone, S. L., "Synthetic Applications of Enantioselective Organotransition-Metal-Mediated Reactions," *Chem. Rev.*, 1989, 89, 1663–1679;

(6) Brunner, H. T., "Enantioselective Synthesis with Optically Active Transition Metals," Chapter 4 in *The Chemistry of the Metal-Carbon-Bond*, Vol. 5, Hartley, ed., John Wiley & Sons: New York, 1989, 109–146;

(7) Brunner, H. T., "Enantioselective Synthesis with Optically Active Transition Metal Catalysts," *Synthesis*, 1988, 645–654; and (8) Merlic, C. A., "Ch. 3. Transition Metal-Mediated Asymmetric Allylic Alkylations," *Molybdenum Catalyzed Allylic Alkylations*, Ph.D., University of Wisconsin, Madison, 1988, pp. 4–79.

Among such transition metal catalyzed bond forming reactions are those involving palladium. One application of this invention is to form cyclopentane analogs of carbohydrates through use of the inventive ligands and palladium. Preparation of mannostatin A exemplifies this class.

For ease of synthesis and high e.e., particularly preferred chiral ligands of the invention for enantioselective catalysis are reaction products derived from 2-diphenylphosphino benzoic acid (2-DPPBA) and either chiral alcohols or chiral amines.

The 2-DPPBA may be derivatized with any of a wide variety of chiral alcohols or chiral amines, preferably by coupling in the presence of dicyclohexylcarbodiimide (DCC), as illustrated by Reaction 2.

REACTION 2

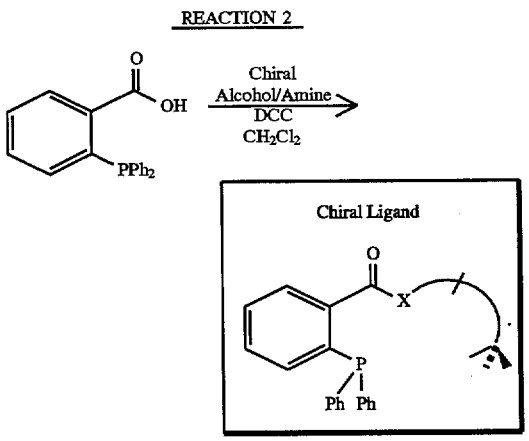

Among the inexpensive and readily available chiral diols useful for derivatizing 2-diphenylphosphinobenzoic are mannitol and tartaric acid.

While a derivatized 2-DPPBA is a particularly preferred manner of practicing the present invention, with 2-DPPBA forming the metal binding moiety of the inventive ligand, other aromatic carboxylic acids can be used so long as the aromatic carboxylic acid carries a diarylphosphino (or a diheteroarylphosphino) substituent. Thus, the necessary phosphino substituent and the carbonyl substituent may be on an aryl or heteroaryl that is further substituted by a moderately or weakly activating or deactivating group, such as with an alkyl group (branched or unbranched) usually with not greater than about ten carbons, a halide, or an alkoxy (e.g., —OCH$_3$, OC$_2$H$_5$, etc.). Alternatively, the single aryl ring exemplified by 2-DPPBA can be replaced with a fused aryl or heteroaryl ring, such as, for example, naphthalene (optionally substituted as just described for the single aryl ring). In such an instance of fused rings, the necessary phosphino substituent and the carboxyl substituent can either be 1,2 on the one ring or can be 1,3 across the two rings. Among the heteroatoms that can form the single or fused heteroaryl ring of the aromatic carboxylic acid from which the inventive ligands may be derived are nitrogen, oxygen, and sulfur. Illustrative, suitable heteroaryl carboxylic acids on which the diarylphosphino (or diheteroarylphosphino) group can be substituted include compounds such as

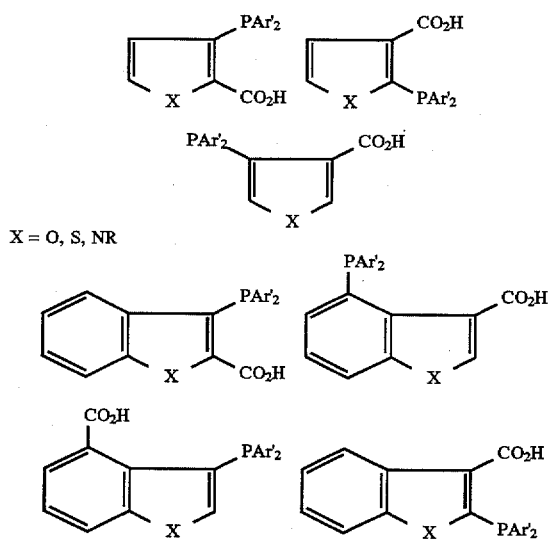

X = O, S, NR

As is illustrated by the preferred embodiment derived from 2-DPPBA, the carboxyl group and the diphenylphosphino group are preferably in an ortho relationship, which serves best for the ligand function.

The carboxylic acid functionality and the alcohol/amine functionalities may be exchanged to generate a new class of ligands that we call "invertomers." The following reactions will illustrate the concept for an amide invertomer ligand.

REACTION 3

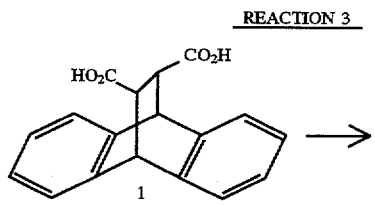

-continued
REACTION 3

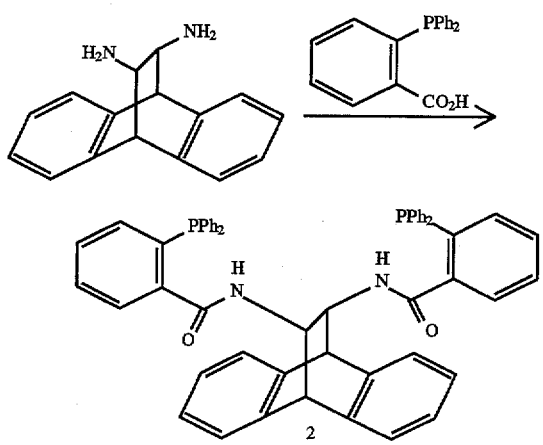

Reaction 3 shows the derivatization of the carboxylic acid to an amine that is to be reacted with 2-DPPBA to form the ligand compound. To make an invertomer, the functionalities of the reactants are swapped. This is illustrated by reaction 4.

REACTION 4

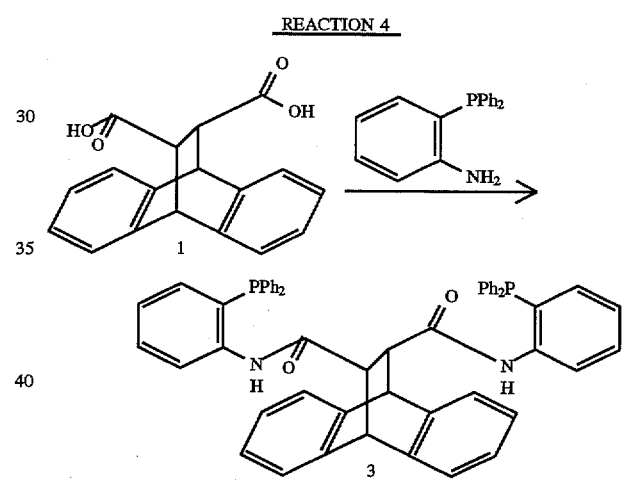

Making an alcohol invertomer will work similarly but with the amine group substituted for an alcohol group.

The particular amide invertomer shown is exciting for two reasons. The invertomers results in the same products as their counterparts but of the opposite chirality as illustrated by reaction 5.

REACTION 5

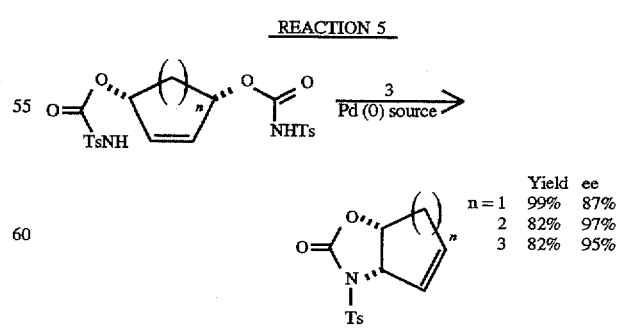

|   | Yield | ee |
|---|---|---|
| n = 1 | 99% | 87% |
| 2 | 82% | 97% |
| 3 | 82% | 95% |

Moreover, the amide invertomer results in the highest e.e. observed for the following reaction with the acyclic substrate.

REACTION 6

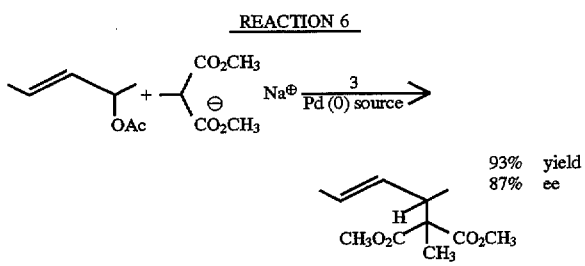

Thus, to summarize, the inventive compounds can be generally described as a functional module (forming a chiral pocket) joined by an ester or an amide linkage to a structural module we term a chiral scaffold. For one class of ligands, the functional module, which is a metal binding component, has the structure

where Ar is an aromatic ring substituent. The functional module is joined by an ester or an amide linkage to the structural module. The structural module can be derived from any chiral alcohol or chiral amine having one or more stereogenic centers. A particularly preferred embodiment of the structural module is derived from a C2 symmetrical bis alcohol or a bis amine.

The invertomers comprise another class of ligands. For invertomers, the functional module is defined by one of the following two structures

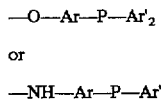

where Ar is an aromatic ring substituent. The functional module is also joined by an ester or an amide linkage to a structural module. However, the structural module is derived from any chiral carboxylic (or dicarboxylic) acid. Similarly, a particularly preferred embodiment of the structural module is derived from a C2 symmetrical bis carboxylic acid.

The choice of a particular chiral alcohol or amine or chiral carboxylic acid, will depend on the circumstances the metal catalyst will be used. The catalytic complex formed by the metal and the inventive compounds are analogous to a crude enzyme. They show enantioselectivities and, in some instances, rate enhancements analogous to enzymes without the substrate specificity exhibited by enzymes. Thus, they are more practical for general chemical synthesis.

The metal catalytic complexes possible with the inventive compounds seek to mimic both the function and specificity of enzymes. The catalytic function is provided by the metal binding moieties and the specificity is provided by the chiral backbone of the structural module. Stereospecificity is possible because the metal binding moieties are positioned in a certain three dimensional orientation by their attachment to stereogenic centers forming a crude version of an enzymatic active site. The three dimensional orientation permitted by a particular scaffold will favor the formation of a particular enantiomeric product in a predictable fashion. Consequently, the choice of a specific structural module will depend on the particular enantiomer that is desired in the product. Other considerations include steric and electronic characteristics of the components to minimize the energy of the conformer with the optimal orientation for metal binding. These considerations are well known in the art and the choice is not unguided. As will be explained in the examples, the preferred stereochemistry of the product is a consequence of the stereochemistry of the ligand. Moreover, rigidity and C2 symmetry are also preferred ligand characteristics because of the resulting decrease in the number of possible transition states. Because the modular nature of the present invention, versatility and increased stereoselectivity are provided as outstanding advantages.

Table 1 summarizes a variety of inventive compounds with single rings in the "Ar" of the metal binding moiety.

TABLE 1

| Inventive Ligand Embodiment | Structure of the Ligand | e.e from Reaction 1 |
|---|---|---|
| (+)-6.24 | 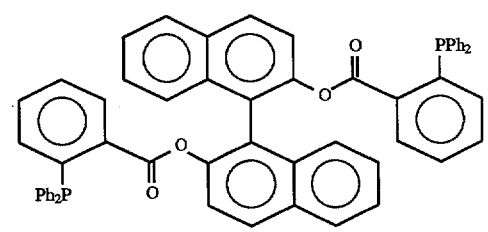 | 40% |

TABLE 1-continued

| Inventive Ligand Embodiment | Structure of the Ligand | e.e from Reaction 1 |
|---|---|---|
| (+)-6.25 | | 64% |
| (−)-6.26 | | 61% |
| (+)-6.27 | | 80% |
| (−)-6.27 | | 79% |

TABLE 1-continued
| Inventive Ligand Embodiment | Structure of the Ligand | e.e from Reaction 1 |
|---|---|---|
| (−)-6.28 | | 78% |
| (+)-6.29 | | 75% |
| (−)-6.31 | | 60% |
| (+)-6.32 | | 88.1% |
A particularly preferred ligand of the invention has the Formula I structure, and is hereinafter sometimes referred to as "(RR)-$L_{12N}$" as an abbreviation of (−)-1R,2R-diamino-1N,2N-bis(2'-diphenylphosphino-1'-nathoyl)cyclohexane.
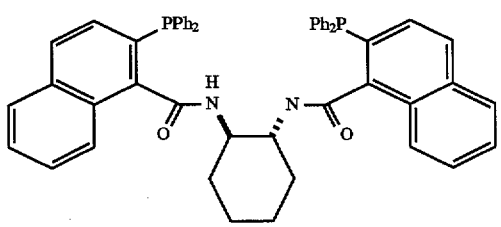
FORMULA I This chiral ligand embodiment has proved remarkably successful in the amination of butadiene monoepoxide, which is a potentially desirable starting material for an asymmetric synthesis providing access to each enantiomer of vinylglycinol. Thus, the ligand (RR)-$L_{12N}$ should prove useful in syntheses of many biologically important targets.

Without being limited by theory, we believe that the (RR)-$L_{12N}$ embodiment has dramatic effects on asymmetric induction by rigidifying the mode of linkage between the chiral scaffold and the "chiral pocket" in which reaction occurs by freezing rotations in the linker. Thus, we believe that the (RR)-$L_{12N}$ ligand has a relatively tight "chiral pocket" formed by the two metal binding moieties held in position by the chiral scaffold. Rigidifying the carboxylate unit by using a ligand constructed from the diamine and 2-diphenylphosphino-1-naphthoic acid had a dramatic effect in enhancing selectivity. This preferred ligand embodiment gave an outstanding result in the addition of phthalimide to 3,4-epoxy-1-butene (butadiene monoepoxide), and provided the protected vinylglycinol quantitatively with an enantiomeric ratio (e.r.) of 99:1. Since vinylglycinol of high enantiomeric purity has now been made available simply through use of the inventive ligand, there is provided a ready entry into either enantiomeric series for syntheses of biologically interesting and important targets.

Our earlier ligand designs had involved the use of acyclic diols to give ligands exemplified by ligand 6.24 (as designated in Table 1). More rigid chiral cyclic diols, such as the ligand derived from the benzyltartriimide, led to even better enantiomeric excess (ligand embodiment 6.29). This is a particularly preferred ligand embodiment from diols because it is derived from the inexpensive and readily available tartaric acid. In general, however, the bis-amide ligands give better e.e. than the bis-esters. We attribute these results to the rigidity of the amide linkage, which tends to freeze rotational freedom at the carbonyl-heteroatom bond.

The invention will now be further illustrated by the following examples describing the preparation of ligand embodiments summarized in Table 1 and by Formula I. Example A exemplifies the (known) preparation of the particularly preferred carboxylic acid precursor, 2-DPPBA. Examples B and C give two alternate general procedures for the preparation of ligands from the 2-DPPBA in a coupling using DCC. Examples 1-8 describe in detail the preparations of the ligands summarized in Table 1. Examples 9-10 illustrate some uses of the inventive ligands. Example 11 illustrates preparation and a use of the (RR)-$L_{12}N$ ligand embodiment.

EXAMPLE A

Preparation of 2-Diphenylphosphinobenzoic Acid, 2-DPPBA

To a 100 mL recovery flask equipped with a reflux condenser containing methyl-2-iodobenzoic acid (4.468 g, 17.05 mmol) under nitrogen was added bis(benzonitrile) palladium dichloride (97.5 mg, 0.254 mmol) followed by anhydrous benzene (34 mL). Trimethylsilyldiphenylphosphine (4.50 mL, 6.17 g, 23.9 mmol) was added and the mixture was stirred at 60° C. for 29 h. More trimethylsilyldiphenylphosphine (1 mL, 1.38 g, 5.34 mmol) was added and stirring was continued at 60° C. for 19 h.

Anhydrous methanol was added (to react with TMSI) and solvent was removed in vacuo. To the residual mixture was added absolute ethanol (25 mL), water (10 mL), and potassium hydroxide (2.909 g, 51.84 mmol). The mixture was stirred under nitrogen at 80° C. for 2.5 h and then allowed to cool to room temperature. Solvent was removed in vacuo and the mixture was taken up in water and washed with ether to remove neutral impurities (discarded the ether layer). The aqueous layer was acidified to pH<1 with concentrated hydrochloric acid and extracted with dichloromethane. The organic layer was dried over magnesium sulfate and solvent was removed in vacuo. The residual solid was adsorbed onto a minimum amount of silica gel. The silica gel was loaded onto a 4.3×14 cm column of silica gel and eluted with 50% ethyl acetate/hexanes (1L) followed by 70% ethyl acetate/hexanes (500 mL).

A small amount of baseline material (TLC) contaminated the product, so the solid was taken up in hot ether (100 mL) and hexanes (ca. 175 mL) was added with gentle warming till the solution became slightly cloudy. Crystallization occurred upon slow cooling under nitrogen to afford 2-diphenylphosphinobenzoic acid as yellow crystals (2.775 g, 53.1%).

EXAMPLE B

General Procedure A for the Preparation of Ligands With 2-diphenylphosphinobenzoic Acid Using DCC To a dry flask containing alcohol or amine, excess 2-diphenylphosphinobenzoic acid, 5 mol % 4-dimethylaminopyridine and dicyclohexylcarbodiimide under nitrogen was added anhydrous solvent (THF or dichloromethane). The resultant yellow chalky mixture was stirred at room temperature until thin layer chromatography indicted complete reaction.

The reaction mixture was filtered through a 2 cm pad of celite (wetted with dichloromethane) and the filter cake was washed twice with an equal volume of dichloromethane. Solvent was removed in vacuo and the residue was chromatographed on silica gel.

EXAMPLE C

General Procedure B for the Preparation of Ligands With 2-diphenylphosphinobenzoic Acid Using DCC To a dry flask containing alcohol or amine, excess 2-diphenylphosphinobenzoic acid, 5 mol % 4-dimethylaminopyridine in anhydrous solvent (THF or dichloromethane) under nitrogen was added dicyclohexylcarbodiimide. The yellow, chalky mixture was stirred at room temperature until thin layer chromatography indicted complete reaction.

The reaction mixture was filtered through a 2 cm pad of celite (wetted with dichloromethane) and the filter cake was washed twice with an equal volume of dichloromethane. Solvent was removed in vacuo and the residue was chromatographed on silica gel.

EXAMPLE 1

(S)-(+)-Bis-[2-(diphenylphosphino)benzoyl]-1,1'-binaphthol, 6.24

(Procedure B)—The reaction was run with S-(−)-1,1'-binaphthol (96.8 mg, 0.338 mmol), 2-diphenylphosphinobenzoic acid (226.5 mg, 0.740 mmol), and dicyclohexylcarbodiimide (0.167 g, 0.809 mmol) in dichloromethane (1.5 mL) for 8 h.

The residue was chromatographed on a 2×11 cm column of silica gel with 15% ethyl acetate/hexanes to give the diester, as a white solid (193.5 mg). The solid was recrystallized from hot dichloromethane/hexanes to give the diester, (S)-BDPPB, 6.25, as white needles (160 mg, 54.9%).

Ligand (S)-(+)-6.24: white needles from dichloromethane/hexane), m.p. 114°–116° C. $R_f$ 0.55 (30% ethyl acetate/hexanes). IR (neat film from $CDCl_3$) 3069, 3056, 3016, 3002, 2932, 2855, 1955 (w), 1901 (w), 1817 (w), 1731 (s), 1585, 1511, 1478, 1463, 1434, 1267, 1245, 1220, 1206, 1137, 1089, 1043, 908, 807, 742, 696, 649 cm$^{-1}$. $^1$H NMR ($CDCl_3$, 400 MHz) δ 7.89 (d, J=8.9 Hz, 2H), 7.85 (d, J=7.9 Hz, 2H), 7.38 (6d, J=6.9, 1.2 Hz, 2H), 7.08–7.30 (m, many H), 7.06 (ddd, J=7.9, 3.7, 1.3 Hz, 2H), 6.98 (td, J=7.5, 1.1 Hz, 2H), 6.75 (ddd, J=6.9, 4.0, 1.2 Hz, 2H), 1.55 ($H_2O$). $^{13}$C NMR ($CDCl_3$, 100 MHz) δ 164.31, 146.73, 141.03 (d, J=27.5 Hz), 137.92 (d, J=11.2 Hz), 137.62 (d, J=11.7 Hz), 134.02, 133.88, 133.82, 133.75, 133.69, 133.61, 133.41, 133.16, 132.66, 132.49, 131.91, 131.36, 130.78, 129.24, 128.55, 128.45, 128.37, 128.28, 127.73, 126.79, 125.89, 125.55, 123.41, 121.88. Anal. Calcd. for $C_{58}H_{40}O_4P_2 \cdot 0.67H_2O$: C: 79.62; H: 4.76; Found: C: 79.64; H: 4.85 and C: 79.58; H: 5.08. $[\alpha]_D$=+55.44 (±0.55)° (c 1.11, dichloromethane).

EXAMPLE 2

(+)-1,2:5,6-Di-O-isopropylidene-3,4,-bis-O-(2'-diphenylphosphinobenzoyl)-D-mannitol, 6.25

(Procedure B)—The reaction was run with (+)-1,2:5,6-di-O-isopropylidene-D-mannitol (0.105 g, 0.400 mmol, Aldrich), 2-diphenylphosphinobenzoic acid (0.269 g, 0.878 mmol), and dicyclohexylcarbodiimide (0.206 g, 0.966 mmol) in dichloromethane (1.4 mL) for 11 h.

The residue was chromatographed on a 2×13 cm column of silica gel with 10% ethyl acetate/hexanes to give the diester 6.25 as a clear oil (44.3 mg, 13.2%).

Ligand 6.25: clear oil. $R_f$ 0.83 (60% ethyl acetate/hexanes). IR (neat film from $CDCl_3$) 3070, 3055, 2987, 2935, 2890, 1724 (s), 1585, 1478, 1463, 1434, 1381, 1372, 1245 (s), 1139, 1245 (s), 1139, 1101, 1066, 1054, 909, 850, 745, 697 cm$^{-1}$. $^1$H NMR ($CDCl_3$, 200 MHz) δ 8.15 (m, 2H, 7.18–7.42 (m, 24H), 6.94 (m, 2H), 5.47 (dt, J=6.0, 1.1 Hz, 2H), 4.07 (q, J=6.1 Hz, 2H), 3.68 (dd, J=8.5, 6.1 Hz, 2H), 3.59 (dd, J=8.6, 6.5 Hz, 2H), 1.21 (s, 6H), 1.20 (s, 6H). $^{13}$C NMR ($CDCl_3$, 50 MHz) δ 165.46, 165.40, 141.71 (d, J=28.8 Hz), 137.97 (d, J=12.3 Hz), 134.53, 134.18 (d, J=20.6 Hz), 134.06 (d, J=21.0 Hz) 133.30 (d, J=18.1 Hz), 132.50, 131.24, 128.811, 128.69, 128.55, 128.43, 109.30, 74.41, 72.40, 65.82, 26.18, 24.96. $[\alpha]_D$=+55.45 (±0.15)° (c 4.29, dichloromethane). HRMS: calc'd for $C_{50}H_{48}O_8P_2$—$CH_3$: 823.2590. Found: 823.2590. FAB MS: Calc'd for $C_{50}H_{49}O_8P_2$ (M+H$^+$): 839.2903. Found: 839.2916.

EXAMPLE 3

(−)-1,3:4,6-Di-O-benzylidene-D-mannitol, Bis-[2-diphenylphosphinobenzoate], Hemietherate Complex, 6.26

(Procedure A)—The reaction was run with 1,3:4,6-di-O-benzylidene-D-mannitol (272 mg, 0.759 mmol), 2-diphenylphosphinobenzoic acid (0.5345 g, 1.745 mmol), and dicyclohexylcarbodiimide (0.396 g, 1.92 mmol) in THF (5.5 mL) for 25 h.

The residue was chromatographed on a 2×12 cm column of silica gel with 5–10% ether/hexanes to afford impure product. The impure product was mixed with hot ether and dichloromethane was added with swirling until the mixture became homogeneous. The solution was stored in a refrigerator (7° C.) allowing the formation of diester 6.26 as clear plates. The crystallization was repeated once more for a total yield of 0.342 g (46.4%) for the 2 crops. The product holds 0.5 mol ether of crystallization tenaciously.

Ligand 6.26: m.p. 125°–127° C. (plates from ether/dichloromethane). $R_f$ 0.59 (30% ethyl acetate/hexanes). IR (neat film from $CDCl_3$) 3069, 3056, 2866, 1955 (w), 1890 (w), 1815 (w), 1722 (s), 1585, 1478, 1463, 1435, 1377, 1312, 1266, 1249, 1224, 1140, 1111, 1058, 1027, 998, 909, 745, 731, 690 cm$^{-1}$. $^1$H NMR ($CDCl_3$, 300 MHz) δ 8.16 (dd, J=7.7, 3.7 Hz, 2H), 7.1–7.5 (m, H), 6.92 (dd, J=7.8, 3.9 Hz, 2H), 5.49 (ddd, J=9.8, 9.2, 5.3 Hz, 2H), 5.24 (s, 2H), 4.215 (d, J=10.4, 5.5 Hz, 2H), 4.10 (d, J=9.5 Hz, 2H), 3.48 (q, J=7.0 Hz, 2H, etherate), 3.23 (t, J=10.4 Hz, 2H), 1.21 (t, J=7.0 Hz, 3H, etherate). $^{13}$C NMR ($CDCl_3$, 50 MHz) δ 165.49 (d, J=2.6 Hz), 140.51 (d, J=7.4 Hz), 137.98, 137.88, 137.77, 137.65, 137.28, 134.60, 134.18, 133.90, 133.73, 133.51, 133.34, 132.59, 131.30, 129.02, 128.79, 128.72, 128.65, 128.1–5 (m), 128.02, 126.23, 100.87, 75.62, 67.30, 62.24. $[\alpha]_D$=−47.83 (±0.39)° (c 1.68, dichloromethane). Anal. Calc'd for $C_{58}H_{48}O_8P_2$: C, 74.51; H, 5.17. Found: C, 74.37; H, 5.55.

EXAMPLE 4A (−)-1R,2R-bis(2'-diphenylphosphinobenzamido)-1,2-diphenylethane, 6.27

(Procedure B)—The reaction was run with (+)-1R, 2R-diphenylethanediamine (0.338 g, 1.59 mmol, $[\alpha]_D$=+103.0 (±0.8)° (c 1.115, methanol), 2-diphenylphosphinobenzoic acid (1.024 g, 3.343 mmol), and dicyclohexylcarbodiimide (0.720 g, 3.493 mmol) in dichloromethane (10 mL) for 4 h.

The residue was chromatographed on a 4×11 cm column of silica gel with 1:3 ether/hexanes (100 mL) then 30% ethyl acetate/hexanes (400 mL) followed by 50% ethyl acetate/hexanes (200 mL) to elute the diamide 6.27 as a glass (0.798 g, 63.5%).

Ligand (−)-6.27: white solid precipitated from dichloromethane with hexanes, m.p. 135°–136° C. $R_f$ 0.61 (60% ethyl acetate/hexanes). IR (neat film from $CDCl_3$) 3410, 3326 (b), 3071, 3046, 2979, 2937, 2873, 1956 (w), 1889 (w), 1818 (w), 1733, 1653 (s), 1586, 1564, 1514 (s), 1459, 1154, 1122, 1091, 1071, 1046, 1028 cm$^{-1}$. $^1$H NMR ($CDCl_3$, 200 MHz) δ 7.64 (m, 2H), 7.15–7.35 (m, 16H), 7.05–7.15 (m, 16H), 6.88–6.93 (m, 6H), 5.37 (m, 2H). $^{13}$C NMR ($CDCl_3$, 100 MHz) δ 169.20, 140.53 (d, J=24.5 Hz), 138.40, 137.69 (d, J=12.2 Hz), 137.34 (d, J=12.0 Hz), 136.77 (d, J=22.4 Hz), 134.34, 133.87 (d, J=20.5 Hz), 133.67 (d, J=21.2 Hz), 130.28, 128.70, 128.48, 128.39, 28.33 (b, >1 signal), 127.91, 127.86, 127.63, 127.49, 59.60. Analysis Calcd. for $C_{52}H_{42}N_2O_2P_2$: C, 79.17; H, 5.37; N, 3.55; P, 7.85. Found: C, 79.17; H, 5.37; N, 3.50; P, 8.24. $[\alpha]_D$=−27.5 (±0.5)° (c 1.63, dichloromethane).

EXAMPLE 4B (+)-1S,2S-bis(2'-diphenylphosphinobenzamido)-1,2-diphenylethane, 6.27

(Procedure B)—The reaction was run with (−)-1S, 2S-diphenylethanediamine (0.338 g, 1.59 mmol, $[\alpha]_D$=+104.0° (c 1.09, methanol), 2-diphenylphosphinobenzoic acid (1.024 g, 3.343 mmol), and dicyclohexylcarbodiimide (0.720 g, 3.493 mmol) in dichloromethane (10 mL) for 6 h.

The residue was chromatographed on a 4×11 cm column of silica gel with 1:3 ether/hexanes (100 mL) then 30% ethyl acetate/hexanes (400 mL) followed by 50% ethyl acetate/hexanes (200 mL) to elute the diamide 6.27 as a glass (0.980 g, 78.0%).

Ligand (+)-6.27: white solid precipitate from dichloromethane with hexanes. $R_f$ 0.61 (60% ethyl acetate/hexanes). $[\alpha]_D=+27.4$ ($\pm 0.6$)° (c 1.62, dichloromethane).

EXAMPLE 5

(−)-1R,2R-Diamino-1N,2N-bis(2'-diphenylphosphinobenzoyl) Cyclohexane, 6.28

(Procedure B)—The reaction was run with (−)-1R, 2R-diaminocyclohexane (0.1312 g, 1.149 mmol, Aldrich), 2-diphenylphosphinobenzoic acid (0.774 g, 2.528 mmol), and dicyclohexylcarbodiimide (0.521 g, 2.528 mmol) in dichloromethane (4 mL) for 9 h.

The residue was chromatographed twice on silica gel with 15–30% ethyl acetate/hexanes (gradient) to give the diamide 6.28 as a glass foam (0.2366 g, 29.8%).

Ligand 6.28: waxy solid precipitated from dichloromethane with hexanes, m.p. 80°–120° C. $R_f$ 0.43 (50% ethyl acetate/hexanes). IR (neat film from $CDCl_3$) 3303, 3070, 2935, 2857, 1955 (w), 1887 (w), 1817 (w), 1645 (s), 1538, 1478, 1434, 1328, 1306, 1162, 1091, 909 cm$^{-1}$. $^1$H NMR ($CDCl_3$, 200 MHz) δ 7.57 (m, 2H), 7.15–7.26 (m, 24H), 6.91 (m, 2H), 6.31 (bd, J=7.7 Hz, 2H, N—H), 3.77 (m, 2H), 1.87 (m, 2H), 1.62 (m, 2H), 0.9–1.3 (m, 6H). $^{13}$C NMR ($CDCl_3$, 50 MHz) δ 169.46, 140.80 (d, J=24.2 Hz), 137.96 (d, J=11.8 Hz), 137.88 (d, J=12.3 Hz), 136.81 (d, J=21.6 Hz), 134.34, 133.97 (d, J=20.3 Hz), 130.23, 128.79, 128.66, 128.57, 128.51, 128.43, 127.63, 127.55, 53.68, 31.71, 24.41. Analysis calcd. for $C_{44}H_{40}N_2O_2P_2$: C, 76.51; H, 5.83; N, 4.06; P, 8.97. Found: C, 76.16; H, 6.28; N, 4.02; P, 8.93. $[\alpha]_D=-46.7$ ($\pm 0.3$)° (c 2.366, dichloromethane).

EXAMPLE 6

(+)-1R, 2R-N-benzyl-2O,3O-bis(2'-diphenylphosphinobenzoyl)tartrimide, 6.29

(Procedure A)—The reaction was run with (+)-1R, 2R-N-benzyltartrimide (0.303 g, 1.37 mmol), 2-diphenylphosphinobenzoic acid (0.922 g, 3.018 mmol), and dicyclohexylcarbodiimide (0.649 g, 3.45 mmol) in THF (5 mL) for 24 h.

The residue was chromatographed on a 2.5×13 cm column of silica gel with 10–20% ethyl acetate/hexanes (gradient) to afford ligand 6.29 as an oil (0.88 g, 70.4%).

Ligand (+)-6.29: clear oil. $R_f$ 0.36 (1:1 ether/hexanes). IR (neat film from $CDCl_3$) 3056, 3070, 2935, 1955 (w), 1888 (w), 1804 (w), 1730 (s), 1586, 1479, 1463, 1435, 1399, 1350, 1332, 1271, 1249, 1171, 1138, 1105, 1069, 1037, 998, 909 cm$^{-1}$. $^1$H NMR ($CDCl_3$, 200 MHz) δ 8.03 (m, 2H), 7.13–7.45 (m, 29H), 6.92 (m, 2H), 4.73 (d, J=14.2 Hz, 1H), 4.58 (d, J=14.2 Hz, 2H). $^{13}$C NMR ($CDCl_3$, 75 MHz) δ 168.94, 165.54, 141.63 (d, J=28.8 Hz), 137.66 (d, J=11.2 Hz), 137.39 (d, J=11.6 Hz), 134.72, 134.46, 134.16 (d, J=20.9 Hz), 134.00 (d, J=20.7 Hz), 132.96, 132.17 (d, J=18.6 Hz), 131.75, 131.72, 128.94 (br), 128.81, 128.77, 129.19 (d, J=4.6 Hz), 128.56, 128.36, 128.23, 73.03, 42.81. $[\alpha]_D=+77.5$ ($\pm 0.3$)° (c 1.025, dichloromethane). Anal. calc'd for $C_{49}H_{37}NO_6P_2$: C, 73.77; H, 4.67. Found: C, 73.50; H, 5.01.

The ligand 6.29 is a particularly preferred embodiment of the invention when prepared from chiral diols because the chiral diol useful as the chiral scaffold in preparing inventive ligand 6.29 is readily derived from tartaric acid via tartrimide. Preparation of the tartrimide from tartaric acid is known and is generally illustrated by Reaction 7 as follows:

REACTION 7

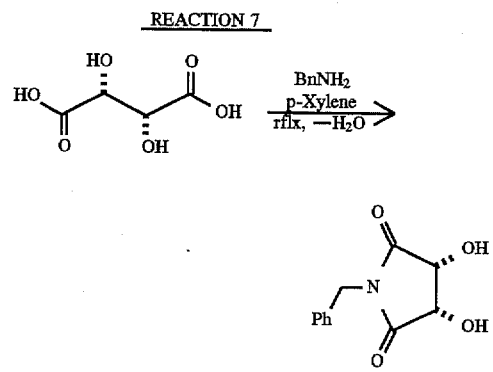

The ligand 6.29 can have Bn as aryl or alkyl (such as, for example, lower alkyl) in addition to benzyl.

EXAMPLE 7

(−)-3-aza-3-benzyl-1R, 5R-dihydroxy-1O, 5O-bis(2'-diphenylphosphinobenzoyl)-1, 5-diphenylpentane, 6.31

(Procedure B)—The reaction was run with 3-aza-3-benzyl-1R, 5R-dihydroxy-1, 5-diphenylpentane (0.223 g, 0.642 mmol), 2-diphenylphosphinobenzoic acid (0.413 g, 1.348 mmol), and dicyclohexylcarbodiimide (0.285 g, 1.38 mmol) in dichloromethane (3 mL) for 36 h.

The residue was chromatographed on a 2.5–14 cm column of silica gel with 5% ethyl acetate/hexanes and then rechromatographed with 5:20:75 ethylacetate/chloroform/hexanes to afford ligand 6.31 as a glass oil (0.179 g, 30.2%).

Ligand (+)-6.31: glass oil. $R_f$ 0.60 (30% ethyl acetate/hexanes). IR (neat film from $CDCl_3$) 3066, 3031, 2957, 2929, 2830, 1952 (w), 1882 (w), 1813 (w), 1716 (s), 1586, 1495, 1478, 1463, 1455, 1434, 1361, 1310, 1268, 1252, 1141, 1106, 1057, 1027, 1002, 965, 909 cm$^{-1}$. $^1$H NMR ($CDCl_3$, 300 MHz) δ 8.05 (m, 2H), 6.85–7.4 (m, 34H), 5.90 (t, J=6.6 Hz, 2H), 3.68 (d, J=4.0 Hz, 2H), 3.47 (d, J=4.0 Hz, 2H), 2.84 (m, 4H). $^{13}$C NMR ($CDCl_3$, 75 MHz) δ 165.98, 140.85, 140.81, 139.23, 138.83, 138.35, 138.18, 138.01, 134.66, 134.44, 134.28, 134.23, 134.01, 133.96, 132.03, 130.98, 128.85, 128.68, 128.59, 128.50, 128.28, 128.17, 128.07, 127.89, 127.79, 127.17, 127.07, 126.73, 74.3, 58.98, 58.52. $[\alpha]_D=-5.04$ ($\pm 0.4$)° (c 1.79, dichloromethane). LSIMS: mle 924 ($M^{3O}$+H, 55), 618 (76), 528 (100).

EXAMPLE 8

(+)-11S,12S-bis (2'-diphenylphosphinobenzamido)-9,10-dihydro-9,10-ethanoanthracene, 6.32

(Procedure B)—The reaction was run with (+)-11S, 12S-diamino-9,10-dihydro-9,10-ethanoanthracene (0.253 g, 1.071 mmol, $[\alpha]_{405}$=+81.3° (c 2.275, methanol )), 2-diphenylphosphinobenzoic acid (0.6887 g, 2.248 mmol), and dicyclohexylcarbodiimide (0.463 g, 2.248 mmol) in dichloromethane (5 mL) for 10 h.

The residue was chromatographed on a 4.5×11.5 cm column of silica gel with 900 mL 30% ethyl acetate/hexanes to give diamide 6.32 as a glass foam (0.860 g, 98.8%).

Ligand (+)-6.32: glass foam. $R_f$ 0.63 (50% ethyl acetate/hexanes). IR (neat film $CDCl_3$) 3418, 3396, 3305 (b), 3070, 3063, 3026, 1955 (w), 1905 (w), 1885 (w), 1818 (w), 1652 (s), 1585, 1505 (s), 1480, 1459, 1327, 1308, 1293, 1250, 1228, 1155, 1124, 1090, 1027, 909 cm$^{-1}$. $^1$H NMR (CDCl$_3$, 200 MHz) δ 7.0–7.45 (m, 34H), 6.95 (m, 2H), 5.72 (bd, J=6.8 Hz, 2H, N—H), 4.42 (d, J=2.4 Hz, 2H), 3.94 (m, 2H). $^{13}$C NMR (CDCl$_3$, 100 MHz) δ 169.00, 141.17 (d, J=26 Hz), 141.028, 136.76 (d, J=12 Hz), 137.36 (d, J=11.6 Hz), 136.45 (d, J=21.5 Hz), 134.54, 133.95 (d, J=20.3H), 133.79 (d, J=20.2 Hz), 130.36, 128.88, 128.79, 128.74, 128.65, 128.63, 127.60 (d, J=5.1 Hz), 126.75, 126.64, 126.03, 124.83. Analysis calcd. for $C_{54}H_{42}N_2O_2P_2$: C, 79.79; H 5.21; N, 3.45. Found: C, 80.01; H 5.28; N, 3.36. $[α]_{405}$=+211.2 (±0.3)° (c 3.35, 26° C., dichloromethane). $[α]_{477}$=+84.7 (±0.3)° (c 3.35, 25° C., dichloromethane).

The enantiomeric excesses obtained with the inventive ligands 6.24 and 6.25 are quite good (up to 64% e.e. for ligand 6.25), with the ligand 6.29 (which is believed to have a further restricted number of degrees of freedom) having a 75% enantiomeric excess. The amides gave even better enantiomeric excesses (about 80–88% e.e.) and are particularly preferred embodiments of the invention.

We have found that $C_2$-symmetrical complexes (that is, the ligands which bind palladium with $C_2$ symmetry) give high orders of enantioselectivity and also permit predictable enantiomeric formation. That is, we have found that the ligand stereochemistry predicts product stereochemistry. Thus, while the stereogenic backbone of the inventive ligands has no direct interaction with the palladium-olefin moiety, the two otherwise independent triphenylphosphines defined by the chiral linkage, or scaffold, serve to organize the aromatic rings into a chiral array and provide a direct relationship for absolute stereochemistry of the product from the catalysis.

Example 9 illustrates a general procedure for palladium catalysis with inventive ligands exemplified by chiral 2-(diphenylphosphino)benzoate esters and amides.

EXAMPLE 9

(Scalemic)-1-p-toluenesulfonylcyclopent-5-eno[4,3-d]-3aS, 6aR-oxazolidin-2-one

To a flask containing a 1M solution of 1R,4S-dihydroxycyclopent-2-ene in anhydrous THF under nitrogen was added p-toluenesulfonylisocyanate (205 mol %) dropwise resulting in an exothermic reaction. The solution was stirred at 50° C. for 1 h.

A dry flask was charged with an inventive chiral ligand (15–20 mol % for monodentate and 7.5 mol % for bidentate ligands) and tris(dibenzylideneacetone)dipalladium(0) chloroform complex (2.5 mol %) under nitrogen and anhydrous THF was added. The black-purple slurry was stirred at room temperature until a homogeneous solution was obtained and then at 50° C. for 10 minutes resulting in a clear, red-orange solution (0.05M in palladium). The catalyst solution was then cooled to 0° C. and the bis-carbamate solution was added dropwise. The reaction was stirred at 0° C. until thin layer chromatograph (50% ethyl acetate/hexanes) indicated complete consumption of bis-carbamate and then solvent was removed in vacuo. The resulting brown-orange oil was directly chromatographed on silica gel with 10–20% ethyl acetate/hexanes (gradient) to afford scalemic oxazolidinone.

The Example 9 procedure was used for each of the inventive ligands reported in Table 1 for product yields up to 100% (through use of ligand 6.25 and ligand 6.31). Inventive ligands were used in the asymmetric synthesis of an intermediate for the synthesis of Mannostatin A (as we reported in Trost and Van Vranken, "A Flexible Strategy to Polyfunctional Cyclopentanes. A Synthesis of Mannostatin A", *J. of Am. Chem. Soc.*, 113, 6317–6318 (1991). Mannostatin A is a highly specific non-toxic inhibitor of α-D-mannosidase, and thus this glycosidase inhibitor has potential as an antiviral agent, as well as possibly an antimedistatic, anti-tumor proliferative, or an immunoregulatory agent. Mannosidase inhibitors, in particular, have been suggested as potential anti-HIV agents.

One preferred mode contemplated for carrying out this invention is building substituted five membered carbocyclic rings with varying substituted patterns with high enantioselectivity. Example 10 illustrates the retrosynthetic analysis for the chemo-, regio-, and diastereoselectivity of introduction of three different heteroatom functions on each and every carbon of a cyclopentane, and thus is a procedure that may be used to make carbanucleoside intermediates asymmetrically since the cyclopentane is a key intermediate towards pseudomonosaccharides. Thus, Example 10 illustrates use of the invention to make a carbanucleoside in which use of inventive ligand 6.28 permitted the excellent enantiomeric excess of 96% $[α]_D^{25}$+111 (c 4.57, CHCl$_3$ (1 mol % (dba)$_3$ Pd$_2$.CHCl$_3$, 3 mol % ligand, THF, quantitative yield) of the 1R,2S enantiomer, as determined by comparison of rotations to a sample whose e.e. was established by the O-methylmandelate ester nmr shifts determined on a transformation product derived therefrom.

Another preferred mode for carrying out this invention is use to obtain vinylglycinol in high enantiomeric purity, which is illustrated by Example 11.

EXAMPLE 10

(+)-3-Benzenesulfonyl-cis-3a-dihydro-4H-cyclopent[d]isoxazole-2-oxide

To a mixture of Pd$_2$(dba)$_3$(CHCl$_3$) (200.0 mg, 0.193 mmol) and chiral ligand 6.27 (320.0 mg, 0.464 mmol), THF (15 mL) was added. The mixture was stirred for 60 minutes and then cooled to 0° C. A solution of 1-cyclopentene-3,5-dibenzoate (5.96 g, 19.4 mmol) and lithium nitronate (4.41 g, 21.3 mmol) in 50 mL of THF (warming was necessary for the dissolution) cooled to 0° C. was cannulated into the catalyst solution over a period of 10 minutes. After 3 hours, the reaction mixture was partitioned between ethyl acetate (300 mL) and aqueous sodium bisulfate (10%, 100 mL). The organic layer was further washed with saturated sodium bicarbonate (100 mL) and saturated sodium chloride solutions, dried (magnesium sulfate) and evaporated in vacuo to give an oil. A solution of the product in 100 mL of 1:1 hexanes and ethyl acetate was filtered through a 10-cm silica gel column, washed with 2:1 hexanes/ethyl acetate to get rid of the black color. The filtrate was evaporated to give a yellow oil which solidified. After recystallization from 30% ether/hexanes, the tilted product was obtained as a white solid (4.84 g, 94.4%). $[α]_D$=111.05° (C=4.57, CHCl$_3$), 96.0% e.e. for this batch. IR (film): 1609, 1583, 1447, 1337, 1199, 1175. $^1$H NMR (300 MHz, CDCl$_3$): δ 7.59–810 (m, 5H), 6.24 (m, 1H), 5.85 (m, 1H), 5.73 (d, J=9.3 Hz) 4.42 (m, 1H), 2.97 (m, 2H). $^{13}$C (75 MH, CDCl$_3$): 138.6, 138.1, 135.3, 129.8, 129.3, 127.9, 120.4, 86.3, 45.5, 38.7. MS: 265 (M+/e,71), 219 (54), 160 (13), 141 (46), 77 (100).

(+)-3-Benzenesulfonyl-cis-3a,6a-dihydro-4H-cyclopent[d]isoxazole-2-oxide

To the above N-oxide (4.75 g, 17.9 mmol) dissolved in 100 mL of acetonitrile was added 10.0 g (3 eg., 52.9 mmol)

of stannous chloride. The suspension was stirred at r.t. for 6 hours. The reaction mixture was filtered through a Celite pad and the filtrate was evaporated. The residue was taken up in ethyl acetate and insoluble materials were again removed by filtration. The ethyl acetate filtrate was washed sequentially with saturated sodium bicarbonate and sodium chloride solutions, dried over magnesium sulfate, and filtered, and the solvent was removed in vacuo. The crude product was purified by flashing chromatography on silica gel, elution with 4:1 hexanes/ethyl acetate to give 4.15 g (93.0%) of the title compound. $[\alpha]_D=183.08°$ (c=4.69, $CHCl_3$). IR (film): 3068, 2929, 2866, 1583, 1561, 1447, 1329, 1311, 1159. $^1$H NMR (300 MHz, $CDCl_3$): δ 8.00 (d, J=7.2 Hz, 1H), 7.74 (t, J=7.15 Hz, 1H), 7.60 (t, J=7.2 Hz, 2H), 6.09 (m, 1H), 5.91 (dd, J=9.3, 1.1 Hz, 1H), 5.82 (m, 1H), 4.20 (td, J=9.6, 1.9 Hz, 1H), 3.10 (dt, J=18.7, 2.0 Hz, 1H), 2.83 (ddt, J=18.7, 8.3, 2.3 Hz, 1H). $^{13}$C (75 MHz, $CDCl_3$): 162.0, 139.0, 135.9, 135.2, 129.9, 129.4, 128.5, 95.7, 48.6, 36.8. MS: 249 (M+/e,11), 220 (44), 143 (27), 108 (68), 77 (100). Anal. Calc'd for $C_{12}H_{11}NO_3S$: C, 57.82; H, 445; N, 5.61; MW, 2249.0160. Found: C, 57.88; H, 4.26; N, 5.51; MW, 249.01060.

(+)-3-Methoxy-cis-3a,6a-dihydro-4H-cyclopent[d]isoxazole-2-oxide

A suspension consisting of the above benzensulfonylisoxazole (4.00 g, 16.1 mmol) and excess well-pulverized potassium carbonate (12.0 g) in anhydrous methanol (80 mL) was heated at reflux for 3 hour. Methanol was removed by evaporation in vacuo. The organic material was taken up in ethyl acetate, washed with dilute sodium chloride solution twice and dried over magnesium sulfate. Filtration and concentration in vacuo gave a clear oil, which was purified by flash chromatography (4:1 hexanes/ethyl acetate as eluent) to afford the title compound (1.90 g, 85.1%). $[\alpha]_D=$ 122.05° (c=3.33, $CHCl_3$). IR (film): 2923, 2852, 1625, 1448, 1368, 1351, 1002. $^1$H NMR (300 MHz, $CDCl_3$): δ 6.01 (dd, J=5.7, 2.8 Hz, 1H), 5.80 (dd, J=5.7, 2.1 Hz, 1H), 5.68 (d, J=8.4 Hz, 1H), 3.85 (s, 3H), 3.73 (ddd, J=8.4, 6.3, 2.9 Hz, 1H), 2.64 (m, 2H). $^{13}$C (75 MHz, $CDCl_3$): 169.4, 133.9, 130.4, 91.4, 57.5, 46.6, 35.5 MS: 139 (100), 124 (37.8), 111 (19.1), 110 (19.9), 106 (22.0), 97 (66.0), 82 (93.0). HRMS: Calc'd for $C_7H_9NO_2$: 139.0633. Meas'd: 139.0628.

(−)-Methyl(1S,2R)-2-hydroxy-3-cyclopentene-1-carboxylate $Mo(CO)_6$ (251 mg, 0.951 mmol) was added to a solution of the above 3-methoxyisoxazoline (240 mg, 1.73 mmol) in acetonitrile/water (30:1, 31 mL) containing 320 mg (5.24 mmol) of boric acid under nitrogen. After heating at reflux for 7 h, silica gel (1.0 g) and methanol (10 mL) were added with stirring continued in the open air for an additional 3 h. The entire mixture was filtered through a plug of silica gel and the latter washed with ethyl acetate. Concentration of the filtrate in vacuo left a dark oil which was chromatographed on silica gel with a gradient elution (3:1 to 1:1 hexanes/ethyl acetate) to afford 205 mg (84%) of the titled hydroxy ester. $^1$H NMR (300 MHz, $CDCl_3$): δ 6.06 (dd, J=5.7, 3.0 Hz, 1H), 5.87 (dd, J=5.7, 4.8 Hz, 1H), 4.97 (bs, 1H, OH), 3.77 (s, 3H), 3.23 (dd, J=7.2 Hz). $^{13}$C (75 MHz, $CDCl_3$): 173.9, 135.2, 132.1, 77.1, 52.1, 47.9, 33.6.

(−)-(1R,2R)-1-Hydroxymethyl-3-cyclopentent-2-ol

To a stirred suspension of lithium aluminum hydride (377 mg, 10.2 mmol) in anhydrous ether (30 mL) was added slowly a solution of the above hydroxyester (414 mg, 2.69 mmol) in 10 mL of ether. The mixture was stirred at rt for an additional hour. Water (377 μL) was added carefully followed by 15% NaOH (377 μL) and more water (1.13 mL). The mixture was stirred vigorously for 1 h, filtered through a plug of celite and washed with ethyl acetate. Filtrate was dried over $MgSO_4$, filtered and concentrated on rotary evaporator to give a clear oil. This product was purified by flash chromatography on silica gel column eluted with 1:1 to 1:3 hexanes/ethyl acetate to afford 291 mg (95% yield) of the title diol $[\alpha]$—130.19° (c: 2.91, $CHCl_3$). IR (film): 3385, 3073, 2924, 2856, 1655, 1615, 1410, 1336, 1307, 1112, 1045, 1010. $^1$H NMR (200 MHz, $CDCl_3$): δ 5.95 (m, 1H), 5.76 (m, 1H), 4.85 (bd, J=7.0 Hz, 1H), 3.73 (dd, J=7.0, 5.3 Hz, 2H), 3.25 (bs, 1H), 2.37 (dd, J=14.1, 8.0 Hz, 1H), 2.27 (dtd, J=8.0, 2.2, 0.8 Hz, 1H), 2.16 (dd, J=14.1, 2.2 Hz, 1H). $^{13}$C (50 MHz, $CDCl_3$): 135.5, 132.5, 77.5, 62.5, 42.4, 33.4. MS: 114 (1.4), 105 (1.5), 96 (99.9), 83 (100), 81 (23.4), 78 (11.9), 73 (3.9), 66 (63). HRMS: Calc'd for $C_6H_{10}O_2$: 114.0681; Meas'd: 114.0697.

(−)-(1R,2R)-1-Methoxycarboxymethyl-2-methoxycarboxy-3-cyclopentene

To a stirred solution of the above diol (226 mg, 1.98 mmol) in THF (6.0 mL) at −78° C. was added slowly n-BuLi (1.5M, 3.30 mL, 4.95 mmol). The mixture was kept at −78° C, methyl chloroformate (461 μL, 5.94 mmol) was added via a syringe. After 20 minutes at −78° C., the dry-ice acetone bath was removed and the temperature allowed to rise to rt. The reaction mixture was poured into 50 mL of ether. The ethereal phase was washed with 10% $NaHSO_4$, saturated $NaHCO_3$ and NaCl solutions, and then dried over $MgSO_4$. Filtration and concentration left a yellow oil, which was purified by flash chromatography (6:1 to 4:1 hexanes/ethyl acetate) to give 445 mg (97% yield) of the bicarbonate $[\alpha]=−153.89°$ (c=3.75, $CHCl_3$). IR (film): 2960, 1746, 1444, 1348, 1331, 1282, 1258, 1121, 948, 792. $^1$H NMR (200 MHz, $CDCl_3$): δ 6.10 (ddd, J=5.6, 2.3, 2.2 Hz, 1H), 5.88 (dd, J=5.6, 2.2 Hz, 1H), 5.55 (d, J=6.8 Hz, 1H), 4.29 (dd, J=10.7, 8.0 Hz, 1H), 4.18 (dd, J=10.7, 7.1 Hz, 1H), 3.73 (s, 3H), 3.70 (s, 3H), 2.69 (ddd, J=8.0, 7.1, 6.8 Hz, 1H), 2.44 (m, 1H), 2.3 (m, 1H). $^{13}$C (50 MHz, $CDCl_3$): 155.8, 155.5, 137.9, 129.0. 82.0, 66.7, 54.7, 54.6, 39.6, 34.3. MS: 230 (<0.1), 202 (<0.1), 154 (7.5), 110 (21.0), 109 (24.8), 95 (37.2), 84 (15.4), 80 (14.1), 79 (96), 78 (100).

9-[(1'R,4'S)-4-(Methoxycarboxymethyl)-2-cyclopenten-1-yl]adenine

To a solution of $Pd(OAc)_2$ (12.0 mg, 0.0536 mmol) in THF (0.5 mL) was added triisopropylphosphite (106 μL, 0.429 mmol), immediately followed by a n-BuLi (1.5M, 107 μL, 0.161 mmol). After 15 minute, adenine (300 mg, 2.22 mmol, predissolved in 2 mL of dry DMSO) and the above bicarbonate (226 mg, 0.983 mmol, dissolved in 1 mL THF) was sequentially added. After stirring at rt for 4 hours, the solvents were removed. The dark residue was taken up in $EtOH$—$CH_2Cl_2$ (2:1), the insoluble materials were filtered off, and the filtrate was concentrated in vacuo. Purification by flash chromatography on silica gel eluted with 10% $EtOH/CH_2Cl_2$ afforded 260 mg (92% yield) of the titled compound. A white solid was obtained after recrystallization from $CH_2Cl_2$ and ether, m.p. 155°–156° C., $[\alpha]_D^{25}=−44.76°$ (c=4.72, $CHCl_3$). IR (KBr): 3300, 3150, 1744, 1676, 1607, 1569, 1475, 1439, 1331, 1305, 1274, 957. $^1$H NMR (300 MHz, $CDCl_3$): δ 8.31 (s, 1H), 7.87 (s, 1H), 6.4 (bs, 2H), 6.11 (ddd, J=5.7, 2.2, 2.0 Hz, 1H), 5.91 (ddd, J=5.7, 2.2, 2.1 Hz, 1H), 4.24 (dd, J=10.8, 5.3 Hz, 1H), 4.13 (dd, J=10.8, 5.2 Hz, 1H), 3.73 (s, 3H), 3.16 (m, 1H), 2.88 (ddd, J=14.1, 8.9, 8.9 Hz, 1H), 1.68 (ddd, J=14.1, 5.7, 5.6 HMz, 1H). $^{13}$C (75 MHz, CDCl$_3$): 156.4, 156.3, 153.6, 153.0, 150.4, 139.4, 137.7, 131.3, 120.3, 70.0, 59.4, 55.3, 44.9, 35.2. Anal. Calc'd for C, 53.97; H, 5.23; N, 24.21; Found: C, 53.86, H, 5.37; N, 24.00.

9-[(1'R,4'S)-4-(Hydroxymethyl)-2-cyclopenten-1-yl] adenine

The above carbonate (105 mg, 0.363 mmol) in 2 mL of ethanol was treated with 0.5 mL of 10% NaOH at rt for 2 hours. The mixture was neutralized with NH$_4$Cl to pH 8 and the solvents were removed in vacuo. The residue was taken up in absolute EtOH and the insoluble salt was removed by filtration. The filtrate was concentrated and then purified by chromatography on silica gel with a gradient elution using 10% to 30% EtOH/CH$_2$Cl$_2$. Recrystallization from absolute methanol gave 82.0 mg (98% yield) of the titled compound as a white solid, m.p. 194°–196° C., $[\alpha]_D^{25}$=–4.57° (c=0.75, EtOH). IR (KBr): 3270, 3150, 3110, 1681, 2661, 1606, 1509, 1478, 1413, 1096. $^1$H NMR (300 MHz, DMSO-d$_6$): δ 19 (s, 1H), 8.13 (s, 1H), 8.13 (s, 1H), 6.21 (dd, J=3.2, 2.3 Hz, 1H), 5.94 (dd, J=5.5, 2.3 Hz, 1H), 5.68 (dd, J=5.5, 4.1 Hz, 1H), 3.61 (m, 2H), 3.02 (m, 1H), 2.88 (ddd, J=9.0, 8.9, 6.9 Hz, 1H), 1.74 (dd, J=13.8, 6.6, 4.9 HMz, 1H). $^{13}$C (75 MHz, DMSO-d$_6$): 157.7, 153.9, 150.6, 141.2, 140.4, 130.8, 120.5, 65.4, 61.4, 49.2, 35.5.

EXAMPLE 11

2-diphenylphosphino-1-naphthoic Acid

To a 250 ml round bottom flask was added 2.85 g (7.7 mmol) 2-diphenylphosphino-1-naphthoic acid methyl ester, 14.8 g (47.0 mmol) Ba(OH)$_2$.8H$_2$O, the flask purged with nitrogen, and 47 ml MeOH added. The reaction was heated at reflux overnight (25 hours). After cooling to room temperature, the reaction mixture was neutralized with 200 ml 1N NaHSO$_4$ (aq) and extracted 4×100 ml dichloromethane. The combined organic phases were dried over Na$_2$SO$_4$ and concentrated in vacuo. The yellow residue was absorbed onto ~8 g silica gel and filtered through a short column of silica gel (4 cm×6 cm, 100% ethyl acetate) to give 2.42 g (88%) of a yellow solid (mp 190°–192° C. dec.) which was used without further purification. R$_f$ 0.56 (100% ethyl acetate). IR (Kbr): 3414, 3074, 3057, 1685, 1434, 1287, 1252 cm$^{-1}$. $^1$H NMR (300 MHz, DMSO-d$_6$) δ 8.0 (d, J=8.2 Hz, 1H), 7.82 (d, J=8.0 Hz, 1H), 7.78 (d, J=8.5 Hz, 1H), 7.5–7.6 (m, 2H), 7.25 (m, 10H), 7.15 (dd, J=8.3, 2.8 Hz, 1H). $^{13}$C NMR (75 MHz, DMSO-d$_6$) δ 170.4 (d, J=3.4 Hz), 141.6 (d, J=38.0 Hz), 137.0 (d, J=10.7 Hz), 133.1 (d, J=19.1 Hz), 132.1, 131.9, 130.7 (d, J=17.0 Hz), 129.6, 129.3, 129.2, 128.9 (d, J=6.9 Hz), 128.7, 128.5, 127.8, 125.5. Analysis: Calc'd for C, 77.52; H, 4.81; P, 8.69. Found: C, 77.38; H, 5.00; P, 8.51.

(–)-1R,2R-diamino-1N,2N-bis(2'-diphenylphosphino-1'-naphthoyl)cyclohexane ("(RR)-L$_{12N}$")

To a 100 ml round bottom flask was added 1.90 g (5.33 mmol) 2-diphenylphosphino-1-naphthoic acid and 42 ml dichloromethane. After cooling to 0° C., 1.78 g (17.6 mmol) triethyl amine was added followed by 1.58 g (5.87 mmol) diphenylchlorophosphite added dropwise over 2–3 minutes. After warming to room temperature over 5 hours, the mixture was transferred via cannula to solution of 304 mg (2.66 mmol) (1R,2R)-diaminocyclohexane and 30.5 mg (0.25 mmol) 4-dimethylaminopyridine in 11 ml dichloromethane and stirred overnight. The reaction mixture was diluted with 50 ml dichloromethane and washed 1×50 ml saturated aqueous sodium bicarbonate and dried over sodium sulfate and concentrated in vacuo. The crude product was purified by flash chromatography on silica gel (4.5 cm×11 cm, 25% ethyl acetate in hexanes) to give 1.07 g (51%) of a white solid which was crystallized from chloroform/hexanes as a white powder (mp 148°–150° C). $[\alpha]_D$=+13.94° (c 1.19, CH$_2$Cl$_2$). R$_f$ 0.64 (50% ethyl acetate in hexanes). IR (solution CDCl$_3$): 3412, 3072, 3057, 2938, 2862, 1648, 1602, 1510, 1435, 1313, 1256, 1237, 1091, 1027 cm$^{-1}$. $^1$H NMR (300 MHz, CDCl$_3$) δ 7.8 (d, J=8.2 Hz, 2H), 7.7 (d, J=9.1 Hz, 2H), 7.6 (d, J=8.9 Hz, 2H), 7.2–7.4 (m, 22H), 7.0 (m, 4H), 6.6 (d, J=5.5 Hz, 2H), 3.8 (m, 2H), 2.3 (m, 2H), 1.7 (m, 2H), 1.2–0.13 (m, 4H). $^{13}$C NMR (75 MHz, CDCl$_3$) δ 169.2 (d, J=4.2 Hz), 142.0 (d, J=34.2 Hz), 136.85 (d, J=11.3 Hz), 136.81 (d, J=11.3 Hz), 133.5 (d, J=19.6 Hz), 133.4 (d, J=19.3 Hz), 133.3, 131.3 (d, J=18.1 Hz), 129.9 (d, J=7.9 Hz), 129.4, 129.2, 128.7, 128.7, 128.6, 128.5, 128.4 (d, J=6.7 Hz), 127.7, 127.2, 126.9, 125.6, 54.7, 31.5, 24.4. Analysis: Calc'd for C, 78.97; H, 5.61; N, 3.54; P, 7.83. Found: C, 78.76; H, 5.86; N, 3.38; P, 7.67.

Asymmetric Alkylation of Butadiene Monoepoxide with Phthalimide

To a 20 ml test tube was added 9.1 mg (0.025 mmol) [η$^3$C$_3$H$_5$PdCl]$_2$, 59.3 mg (0.075 mmol) (–)-1R,2R-diamino-1N,2N-bis(2'-diphenylphosphino-1'-naphthoyl)cyclohexane, 5.0 mg (0.05 mmol) sodium carbonate, and 162 mg (1.10 mmol) phthalimide. The flask was purged with nitrogen, 10 ml dichloromethane added, and stirred 10 minutes, color to bright yellow. Then, 70.1 mg (1.00 mmol) butadiene monoepoxide (3) was added, color to clear, and the reaction stirred at room temperature for 2.5 hours at which time the bright yellow color had returned. The reaction mixture was concentrated in vacuo and purified by flash chromatography on silica gel (3 cm×12 cm, 60% diethyl ether in hexanes) to give 216.2 mg (99%) of the 1,3 addition product as a white solid (mp 61°–62° C.) in 98% ee as determined by HPLC of the (S)-methoxyphenylacetate ester. $[\alpha]_D$=–71.11° (c 3.06, CH$_2$Cl$_2$). R$_f$ 0.65 (100% diethyl ether). IR (film from CDCl$_3$): 3450, 3086, 2945, 2888, 1767, 1704, 1644, 1614, 1469, 1386, 1226, 1173, 1107, 1060, 1020 cm$^{-1}$. $^1$H NMR (300 MHz, CDCl$_3$) 7.8 (m, 2H), 7.7 (m, 2H), 6.1 (ddd, J=17.3, 10.2, 6.9 Hz, 1H), 5.3 (m, 2H), 4.9 (m, 1H), 4.1–4.2 (m, 1H), 3.9–4.0 (m, 1H), 2.9 (bs, 1H). $^{13}$C NMR (75 MHz, CDCl$_3$) 168.4, 133.9, 132.0, 131.4, 123.0, 118.6, 61.7, 55.5. Analysis: Calc'd for C, 66.35; H, 5.11; N, 6.45. Found: C, 66.60; H, 5.33; N, 6.65.

Preparation of 2-phthalamido-3-butenyl (S)-methoxyphenylacetate

To a 3 ml test tube was added 10.9 mg (0.05 mmol) 2-phthalamido-3-butenol, 10.1 mg (0.06 mmol) (S)-methoxyphenylacetic acid, 14.4 mg (0.07 mmol) dicyclohexylcarbodiimide, 0.5 mg (0.005 mmol) 4-dimethylaminopyridine, and 0.5 ml dichloromethane. The reaction was stirred at room temperature overnight and then filtered through cotton. The product was purified by flash chromatography on silica gel (1 cm×12 cm, 40% diethyl ether in pentane) to give 18.0 mg (98%) of the title compound as a clear oil in 98% de. as determined by HPLC analysis (Dynamax 60A analytical, 15% ethyl acetate in hexanes, 1.0 ml/min, λ=254 nm, T$_R$=22.3, 23.4 min). $[\alpha]_D$=+4.24° (c 1.80, CH$_2$Cl$_2$). R$_f$ 0.62 (30% ethyl acetate in hexanes). Spectral data taken from racemate (RB-XI-8) IR (film from $CDCl_3$): 3064, 3032, 2990, 2933, 2830, 1756, 1714, 1468, 1455, 1385, 1256, 1174, 1113, 1013 $cm^{-1}$. $^1H$ NMR (300 MHz, $CDCl_3$) 7.7–7.8 (m, 4H), 7.2 (m, 2H), 7.0 (m, 3H), 6.0–6.15 (m, 1H), 5.3 (m, 2H), 5.0 (m, 1H), 4.7 (m, 2H), 4.4 (dd, J=11.0, 5.3 Hz, 1H), 3.33 (s, 3H). $^{13}C$ NMR (75 MHz, $CDCl_3$) 170.0, 167.4, 135.8, 133.9, 131.6, 130.8, 128.4, 128.2, 126.8, 123.3 120.1, 82.1, 63.1, 57.3, 52.1. Analysis: Calc'd for C, 69.03; H, 5.24; N, 3.83. Found: C, 68.88; H, 5.41; N, 3.98.

It is to be understood that while the invention has been described above in conjunction with preferred specific embodiments, the description and examples are intended to illustrate and not limit the scope of the invention, which is defined by the scope of the appended claims.

It is claimed:

1. A chiral compound comprising:

a chiral backbone to which is bound two or three metal binding moieties, the chiral compound capable of participating as a ligand or a chiral auxiliary for metal catalyzed reactions, each metal binding moiety having the following structure $$-\overset{O}{\underset{\|}{C}}-Ar-P-Ar'_2,$$

wherein Ar and Ar' each is an aryl or a heteroaryl with a single ring or fused rings, each metal binding moiety being attached by an ester or an amide linkage to the chiral backbone.

2. The compound as in claim 1 wherein the chiral backbone is derived from a chiral bis-alcohol or a chiral bis-amine and each metal binding moiety is attached by an ester linkage to each of the alcohol functionalities in the chiral bis-alcohol or is attached by an amide linkage to each of the amine functionalities in the chiral bis-amine.

3. The compound as in claim 1 or 2 having $C_2$ symmetry.

4. The compound as in claim 1 wherein Ar' is a phenyl and Ar is an aryl or a heteroaryl with fused rings, wherein when Ar is a heteroaryl with fused rings then the metal binding moiety has a structure selected from the group consisting of

[structures shown]

where X is an oxygen, sulfur or nitrogen heteroatom.

5. The compound as in claim 1 or 2 having the following structure

[structure shown]

wherein the CS is the chiral backbone derived from bis-alcohol or bis-amine, X is O or is NH, and R is H, or a $C_1$–$C_{10}$ alkyl, a halide, or a lower alkoxy substituent.

6. A method for preparing ligands, useful for transition metal catalyzed bond forming reactions, comprising:

providing an aromatic carboxylic acid having a diarylphosphino or a diheteroarylphosphino substituent on the aromatic ring; and forming an ester or an amide derivative of the carboxylic acid by coupling with a chiral diol or a chiral diamine in the presence of dicyclohexylcarbodiimide.

7. The method as in claim 6 wherein the phosphino substituent is ortho with respect to the carbonyl group of the carboxylic acid.

8. The method as in claim 6 wherein the aromatic carboxylic acid has a plurality of fused rings.

9. The method as in claim 6 wherein the ring of the aromatic carboxylic acid includes a heteroatom.

10. A ligand having the following structure:

[structure shown]

wherein Ph is phenyl.

* * * * *

UNITED STATES PATENT AND TRADEMARK OFFICE
CERTIFICATE OF CORRECTION

PATENT NO. : 5,739,396

DATED : April 14, 1998

INVENTOR(S) : Barry M. Trost; David L. Van Vranken; Richard C. Bunt

It is certified that error appears in the above-identified patent and that said Letters Patent is hereby corrected as shown below:

On Column 8, Table 1, at about line 50:

Replace: "

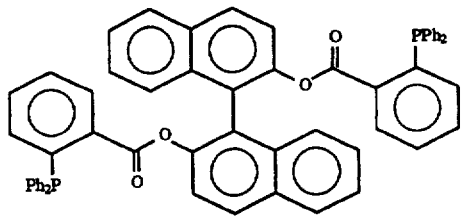

With: --

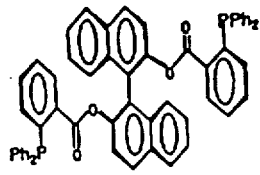

UNITED STATES PATENT AND TRADEMARK OFFICE
CERTIFICATE OF CORRECTION

PATENT NO. : 5,739,396

DATED : April 14, 1998

INVENTOR(S) : Barry M. Trost; David L. Van Vranken; Richard C. Bunt

It is certified that error appears in the above-identified patent and that said Letters Patent is hereby corrected as shown below:

On Column 9, Table 1, at about line 47:

Replace: "

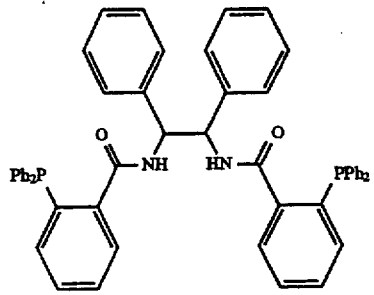

With: --

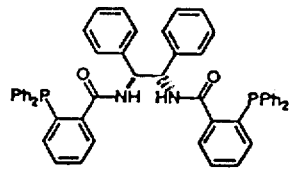

UNITED STATES PATENT AND TRADEMARK OFFICE
CERTIFICATE OF CORRECTION

PATENT NO. : 5,739,396

DATED : April 14, 1998

INVENTOR(S) : Barry M. Trost; David L. Van Vranken; Richard C. Bunt

It is certified that error appears in the above-identified patent and that said Letters Patent is hereby corrected as shown below:

On Column 9, Table 1, at about line 60:

Replace: "

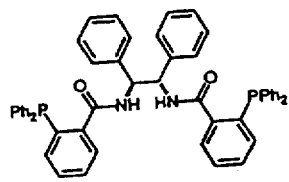

With: --

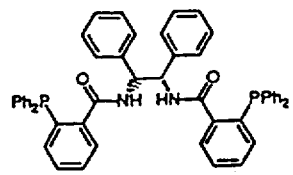

UNITED STATES PATENT AND TRADEMARK OFFICE
CERTIFICATE OF CORRECTION

PATENT NO. : 5,739,396
DATED : April 14, 1998
INVENTOR(S) : Barry M. Trost; David L. Van Vranken; Richard C. Bunt It is certified that error appears in the above-identified patent and that said Letters Patent is hereby corrected as shown below:

On Column 11, Table 1, at about line 7:

Replace: "

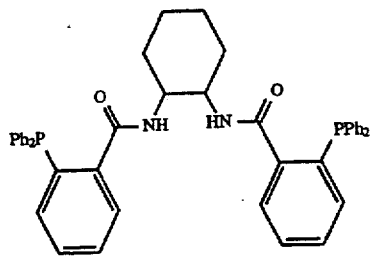

With: --

(+)-6.28

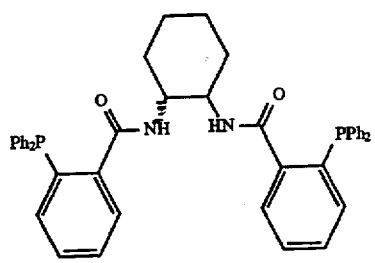

UNITED STATES PATENT AND TRADEMARK OFFICE
CERTIFICATE OF CORRECTION

PATENT NO. : 5,739,396
DATED : April 14, 1998
INVENTOR(S) : Barry M. Trost; David L. Van Vranken; Richard C. Bunt It is certified that error appears in the above-identified patent and that said Letters Patent is hereby corrected as shown below:

On Column 11, Table 1, at about line 20:

Replace: "   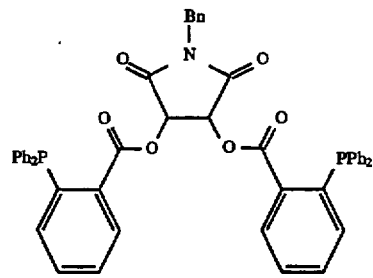

With:   --   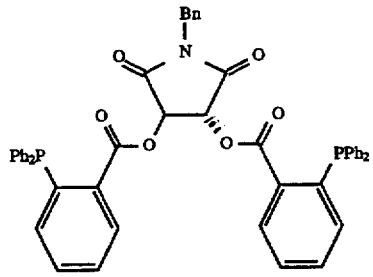

UNITED STATES PATENT AND TRADEMARK OFFICE
CERTIFICATE OF CORRECTION

PATENT NO. : 5,739,396
DATED : April 14, 1998
INVENTOR(S) : Barry M. Trost; David L. Van Vranken; Richard C. Bunt It is certified that error appears in the above-identified patent and that said Letters Patent is hereby corrected as shown below:

On Column 18, Reaction 7, at about line 13:

Replace: "  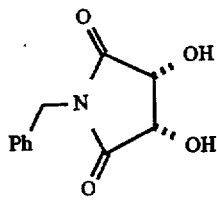

With: --  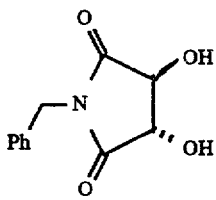

UNITED STATES PATENT AND TRADEMARK OFFICE
CERTIFICATE OF CORRECTION

PATENT NO. : 5,739,396
DATED : April 14, 1998
INVENTOR(S) : Barry M. Trost; David L. Van Vranken; Richard C. Bunt It is certified that error appears in the above-identified patent and that said Letters Patent is hereby corrected as shown below:

On Column 26, Claim 10, line 52:

Replace: "

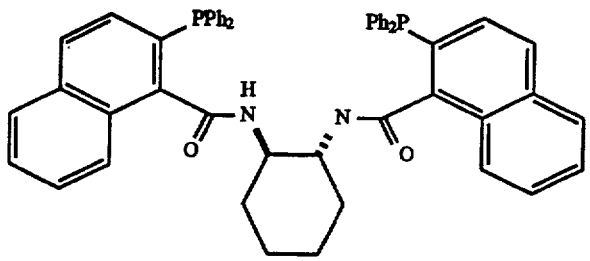

With: --

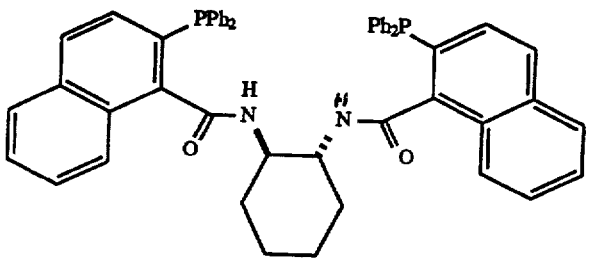

Signed and Sealed this

Seventh Day of November, 2000

Attest:

Q. TODD DICKINSON

*Attesting Officer*     *Director of Patents and Trademarks*